US009309157B2

(12) United States Patent
Fujisaki et al.

(10) Patent No.: US 9,309,157 B2
(45) Date of Patent: Apr. 12, 2016

(54) TRANSLUCENT ZIRCONIA SINTERED BODY, PROCESS FOR PRODUCING THE SAME, AND USE OF THE SAME

(71) Applicants: Hiroyuki Fujisaki, Shunan (JP); Kiyotaka Kawamura, Shunan (JP); Kohei Imai, Shunan (JP)

(72) Inventors: Hiroyuki Fujisaki, Shunan (JP); Kiyotaka Kawamura, Shunan (JP); Kohei Imai, Shunan (JP)

(73) Assignee: TOSOH CORPORATION, Shunan-shi (JP)

(*) Notice: Subject to any disclaimer, the term of this patent is extended or adjusted under 35 U.S.C. 154(b) by 0 days.

(21) Appl. No.: 14/473,494

(22) Filed: Aug. 29, 2014

(65) Prior Publication Data

US 2014/0370453 A1    Dec. 18, 2014

Related U.S. Application Data

(62) Division of application No. 12/936,484, filed as application No. PCT/JP2009/057207 on Apr. 8, 2009, now abandoned.

(30) Foreign Application Priority Data

Apr. 9, 2008  (JP) ................................. 2008-101324
Dec. 24, 2008  (JP) ................................. 2008-328498
Dec. 24, 2008  (JP) ................................. 2008-328499
Dec. 24, 2008  (JP) ................................. 2008-328500

(51) Int. Cl.
| | |
|---|---|
| *C04B 35/48* | (2006.01) |
| *A61C 7/14* | (2006.01) |
| *A61C 13/00* | (2006.01) |
| *C04B 35/486* | (2006.01) |
| *C04B 35/626* | (2006.01) |
| *C01G 25/00* | (2006.01) |
| *C01G 25/02* | (2006.01) |
| *B82Y 30/00* | (2011.01) |
| *A61C 13/083* | (2006.01) |

(52) U.S. Cl.
CPC . *C04B 35/48* (2013.01); *A61C 7/14* (2013.01); *A61C 13/0022* (2013.01); *A61C 13/083* (2013.01); *B82Y 30/00* (2013.01); *C01G 25/00* (2013.01); *C01G 25/02* (2013.01); *C04B 35/486* (2013.01); *C04B 35/62675* (2013.01); *C01P 2002/52* (2013.01); *C01P 2002/54* (2013.01); *C01P 2004/62* (2013.01); *C01P 2006/10* (2013.01); *C01P 2006/12* (2013.01); *C04B 2235/3217* (2013.01); *C04B 2235/3225* (2013.01); *C04B 2235/444* (2013.01); *C04B 2235/5409* (2013.01); *C04B 2235/5436* (2013.01); *C04B 2235/5445* (2013.01); *C04B 2235/5454* (2013.01); *C04B 2235/656* (2013.01); *C04B 2235/6562* (2013.01); *C04B 2235/72* (2013.01); *C04B 2235/765* (2013.01); *C04B 2235/77* (2013.01); *C04B 2235/785* (2013.01); *C04B 2235/96* (2013.01); *C04B 2235/9615* (2013.01); *C04B 2235/9653* (2013.01); *C04B 2235/9669* (2013.01)

(58) Field of Classification Search
CPC ................. C04B 35/48; C04B 35/486; C04B 2235/9653; A61L 27/10; A61C 7/12; A61C 7/16

See application file for complete search history.

(56) References Cited

U.S. PATENT DOCUMENTS

| | | | |
|---|---|---|---|
| 4,758,541 A | 7/1988 | Tsukuma | |
| 4,772,576 A | 9/1988 | Kimura et al. | |
| 4,985,229 A | 1/1991 | Obitsu et al. | |
| 5,279,995 A | 1/1994 | Tanaka et al. | |
| 6,087,285 A | 7/2000 | Oomichi et al. | |
| 7,465,431 B2 | 12/2008 | Katusic et al. | |
| 2002/0031675 A1 | 3/2002 | Cales et al. | |
| 2003/0010659 A1 | 1/2003 | Hernandez | |
| 2010/0003630 A1 | 1/2010 | Yamashita et al. | |

FOREIGN PATENT DOCUMENTS

| | | |
|---|---|---|
| EP | 0 401 999 A2 | 12/1990 |
| EP | 0 420 284 A2 | 4/1991 |

(Continued)

OTHER PUBLICATIONS

Machine translation of JP 2005-211101, Nov. 2005.*

(Continued)

*Primary Examiner* — Karl Group
(74) *Attorney, Agent, or Firm* — Westerman, Hattori, Daniels & Adrian, LLP

(57) ABSTRACT

A subject of the invention relates to providing a powder for a translucent zirconia sintered body which is necessary for the production of a zirconia sintered body having a high sintered-body density and high strength and giving an excellent sense of translucency, without conducting any special sintering, such as HIP sintering. The invention relates to a technique for obtaining, through normal-pressure sintering, a translucent zirconia sintered body characterized by comprising zirconia which contains 2-4 mol % yttria as a stabilizer and has an alumina content of 0.2 wt % or lower, and by having a relative density of 99.8% or higher and a total light transmittance, as measured at a thickness of 1.0 mm, of 35% or higher. It is preferred that a powder containing 0-0.2 wt % alumina with a particle diameter of 0.01-0.5 μm, having a BET specific surface area of 5-16 $m^2/g$ and an average particle diameter of 0.3-0.7 μm, and having a rate of sintering shrinkage in normal-pressure sintering ($\Delta\rho/\Delta T$; $g/cm^{3.\circ}$ C.) of 0.0125 or higher but 0.0160 or lower should be subjected to normal-pressure sintering in the atmosphere.

14 Claims, 4 Drawing Sheets

(56) References Cited

FOREIGN PATENT DOCUMENTS

| | | | |
|---|---|---|---|
| JP | 62-091467 A | 4/1987 | |
| JP | 3-174356 A | 7/1991 | |
| JP | 4-367513 A | 12/1992 | |
| JP | 6-157037 A | 6/1994 | |
| JP | H08-117248 A | 5/1996 | |
| JP | 8-325057 A | 12/1996 | |
| JP | 2000-169222 A | 6/2000 | |
| JP | 2002-255556 A | 9/2002 | |
| JP | 2003-530970 A | 10/2003 | |
| JP | 2004-115343 A | 4/2004 | |
| JP | 2004-143031 A | 5/2004 | |
| JP | 2004-269331 A | 9/2004 | |
| JP | 2005-211101 A | 8/2005 | |
| JP | 2008-024555 A | 2/2008 | |
| JP | 2008-050247 A | 3/2008 | |
| JP | 2008050246 | * | 3/2008 |
| JP | 2008-081325 A | 4/2008 | |
| JP | 2008-222450 A | 9/2008 | |
| WO | 01/80917 A2 | 11/2001 | |
| WO | 2008/013099 A1 | 1/2008 | |

OTHER PUBLICATIONS

International Search Report of PCT/JP2009/057207, mailing date Jul. 21, 2009.
Chinese Office Action dated Sep. 28, 2012, issued in corresponding Chinese Patent Application No. 200980112643.2, with English translation (15 pages).
Extended European Search Report dated Feb. 15, 2013, issued in corresponding European patent application No. 09729325.2.
Anselmi-Tamburini, et al., "Transparent Nanometric Cubic and Tetragonal Zirconia Obtained by High-Pressure Pulsed Electric Current Sintering", Advanced Functional Materials, vol. 17, No. 16, p. 3267-3273, Nov. 5, 2007.
Richard Baker Harrison Ltd, "Tosoh Zirconic Powder", Web URL: http://www.rbhltd.com/rbh_news/wp-content/uploads/2012/01/Powder-Sales-Spec-3YE-2005.pdf, Aug. 19, 2004 (13 pages).
Chinese Office Action dated Aug. 8, 2013, issued in corresponding Chinese Patent Application No. 200980112643.2 with English translation (15 pages).
Extended European Search Report dated Nov. 7, 2013 in corresponding European Patent Application No. 13184318.7.
European Office Action issued Nov. 5, 2013 in corresponding European Patent Application No. 09729325.2.
Japanese Office Action dated Dec. 3, 2013, issued in Japanese Patent Application No. 2008-328498, w/English translation, (12 pages).
Japanese Office Action dated Jan. 7, 2014, issued in corresponding Japanese application No. 2008-328499, w/English translation (12 pages).
Japanese Office Action dated Jan. 7, 2014, issued in corresponding Japanese application No. 2008-328500, w/English translation (14 pages).
Chinese Office Action dated Feb. 13, 2014, issued in corresponding Chinese application No. 200980112643.2, w/English translation (16 pages).
Office Action dated Apr. 1, 2014, issued in Japanese Patent Application No. 2008-328498 with English Translation (7 pages).
Office Action dated Apr. 1, 2014, issued in Japanese Patent Application No. 2008-328499 with English Translation (8 pages).
Office Action dated May 27, 2014, issued in Corresponding Japanese Patent Application No. 2008-328500, with English Translation (11 pages).
U.S. Office Action dated Feb. 22, 2012, issued in related U.S. Appl. No. 12/936,484.
U.S. Office Action dated Sep. 7, 2012, issued in related U.S. Appl. No. 12/936,484.
U.S. Office Action dated May 31, 2013, issued in related U.S. Appl. No. 12/936,484.
U.S. Office Action dated Sep. 12, 2013, issued in related U.S. Appl. No. 12/936,484.
U.S. Office Action dated Dec. 24, 2013, issued in related U.S. Appl. No. 12/936,484.
U.S. Office Action dated Apr. 3, 2014, issued in related U.S. Appl. No. 12/936,484.
Communication Pursuant to Rule 114(2) EPC dated Jan. 13, 2015, issued in European Patent Application No. 13184318.7 (7 pages).
Communication Pursuant to Rule 114(2) EPC dated Jan. 15, 2015, issued in European Patent Application No. 09729325.2 (8 pages).
Matsui, Roji, "Initial Sintering Mechanism of 3 mol% Yttria-doped Zirconia Powder: Effect of Alumina", Tosoh Research & Technology Review, vol. 51, (No. 88), published on Dec. 31, 2007, 20 pages with English translation.
Matsui, Koji et al., "Effect of Added Alumina on the Initial Sintering of Fine Zirconia Powder", Collective works of Proceeding of Debate on Reactivity of Solids, vol. 13, 2002, pp. 113-115 with a partial English translation.
Yamakawa, T, et al., "Sintering behavior of zirconia fine powder", Collectiveworks of Annual Meeting of the Ceramic Society of Japan, vol. 2002, 2002, pp. 266 with a partial English Translation.
Sang, Shiro, "Prerequisites for Translucent Ceramics", Ceramics 16, 1981, No. 6, pp. 462-467 with English translation (7 pages).
Ohmichi et al., "Phase Transformation of Zirconia Ceramics by Annealing in Hot Water", Journal of Ceramic Society of Japan, 107 [2], 1999, pp. 128-133, with partial English Translation (NPL1).
Transformation Strengthening of Ceramics, 1992, pp. 192-193, with partial English Translation (NPL2).
Optoceramics (1934), pp. 74-83 and 112-113, with English translations of cited portions. (NPL1).
Sintering of Ceramics, (1995), pp. 120-125 and 129-131, with English translations of cited portions (NPL2).
Zirconia Ceramics 10, (1989), pp. 123-134, with English translations of cited portions. (NPL3).
Hachiro Hashimoto et al., Study on Zirconia Toughened Ceramics—Preparation of Tetragonal Zirconia Toughened Mullite-, Research Bulletin of Fukui University of Technology, (2001), p. 285-291, with English translations of cited portions. (NPL4).

* cited by examiner

TRANSLUCENT ZIRCONIA SINTERED BODY, PROCESS FOR PRODUCING THE SAME, AND USE OF THE SAME

TECHNICAL FIELD

This application is a divisional of U.S. application Ser. No. 12/936,484, now abandoned, filed on Oct. 5, 2010, which is a National Stage of International Application No. PCT/JP2009/057207, filed on Apr. 8, 2009, which claims priority to Japanese priority application No. 2008-101324 filed on Apr. 9, 2008, Japanese priority application No. 2008-328498 filed on Dec. 24, 2008, Japanese priority application No. 2008-328499 filed on Dec. 24, 2008 and Japanese priority application No. 2008-328500 filed on Dec. 24, 2008, which are hereby incorporated by reference.

The present invention relates to a zirconia sintered body produced by normal-pressure sintering, having a high sintered-body density and high strength, and having excellent translucency. More particularly, the invention relates to a zirconia sintered body for use in dental applications, which is suitable for use as a mill blank for a denture material or the like or as an orthodontic bracket.

BACKGROUND ART

Zirconia sintered bodies containing a small amount of $Y_2O_3$ in a solid solution state as a stabilizer have high strength and high toughness and are hence extensively utilized as materials for machine structures, such as cutting tools, dies, nozzles, and bearings, and materials for the living body, such as dental materials. In the case of dental materials, not only mechanical properties, i.e., high strength and high toughness, but also optical properties, i.e., translucency and color tone, are required from an aesthetic standpoint.

Single crystals of zirconia give a sense of translucency, and single-crystal zirconia containing about 10 mol % yttria (cubic zirconia), which is used as jewelry and the like, has conventionally had a problem that the strength thereof is exceedingly low. On the other hand, it is known that ordinary zirconia sintered bodies, which are polycrystalline objects, do not give a sense of translucency. It is known that the lack of translucency is due to the light scattering caused by voids present between the crystal grains and within the grains. Investigations have hence been made hitherto on techniques for imparting translucency to a polycrystalline zirconia sintered body by diminishing voids, i.e., by increasing the density of the sintered body.

For example, patent document 1 discloses translucent zirconia containing 2 mol % or more $Y_2O_3$ and 3-20 mol % $TiO_2$. However, this translucent zirconia has had a problem concerning strength because this zirconia contains a large amount of $TiO_2$ incorporated in order to impart translucency.

Patent document 2 discloses a zirconia sintered body having a sintered-body density of 99.8%, which has a composition including 3 mol % $Y_2O_3$ and 0.25 wt % $Al_2O_3$ and has translucency. It has been reported that this sintered body has a total light transmittance with respect to visible light of 49% (thickness, 0.5 mm) However, this sintered body is a sintered body obtained by pressure sintering using hot isostatic pressing (HIP), and sufficient translucency has not been obtained in sintered bodies obtained by normal-pressure sintering.

PRIOR-ART DOCUMENTS

Patent Documents

Patent Document 1: JP-A-62-91467
Patent Document 2: JP-A-20-50247

SUMMARY OF THE INVENTION

Problem that the Invention is to Solve

An object of the invention is to provide a zirconia sintered body which eliminates the drawback of the conventional methods described above and which has a high sintered-body density and high strength and has excellent translucency. Another object is to provide a simple process capable of producing such a zirconia sintered body through normal-pressure sintering.

Means for Solving the Problem

The present inventors made detailed investigations on relationships between the state of alumina in a zirconia powder and each of sintered-body density and the total light transmittance of the sintered body. As a result, they have found that for obtaining a translucent zirconia sintered body through normal-pressure sintering, it is necessary to not only enhance the sinterability of a zirconia powder but also control the rate of sintering of the zirconia in a specific temperature range. It has also been found that by controlling the rate of sintering on the basis of the properties of the alumina to be used as an additive, translucent zirconia is obtained through normal-pressure sintering. Furthermore, it has been found that also in the case of yttria-containing zirconia containing no alumina, translucent zirconia is obtained through normal-pressure sintering by controlling the rate of sintering. The invention has been thus completed.

Namely, essential points of the invention reside in the following 1) to 15).

1) A translucent zirconia sintered body characterized by comprising zirconia which contains 2-4 mol % yttria as a stabilizer and has an alumina content of 0.2 wt % or lower, and by having a relative density of 99.8% or higher and a total light transmittance, as measured at a thickness of 1.0 mm, of 35% or higher.
2) The translucent zirconia sintered body according to 1) above which preferably has an alumina content of 0.1-0.2 wt %.
3) The translucent zirconia sintered body according to 1) above which preferably has an alumina content lower than 0.1 wt %.
4) The translucent zirconia sintered body according to 1) above which preferably contains no alumina (has an alumina content of 0 wt %).
5) The translucent zirconia sintered body according to any one of 1) to 4) above which preferably has a crystal grain diameter of 0.20-0.45 μm.
6) The translucent zirconia sintered body according to any one of 1) to 5) above which preferably has a monoclinic fraction of 30% or lower after 24-hour immersion in 140° C. hot water.
7) The translucent zirconia sintered body according to any one of 1) to 6) above which preferably has a three-point bending strength of 1,000 MPa or higher.
8) A powder for a translucent zirconia sintered body, which is a powder containing 2-4 mol % yttria as a stabilizer, having an alumina content of 0.2 wt % or lower, and having a rate of sintering shrinkage (Δρ/ΔT; g/cm$^3$·° C.), in a relative-density range of 70% to 90% in normal-pressure sintering (in the atmosphere, 300° C./hr), of 0.0120 or higher but 0.0160 or lower.

9) The powder for a translucent zirconia sintered body according to 8) above which preferably is a powder containing 2-4 mol % yttria as a stabilizer, containing 0.1-0.2 wt % alumina, and having a rate of sintering shrinkage (Δρ/ΔT; g/cm$^3$·° C.), in a relative-density range of 70% to 90% in normal-pressure sintering (in the atmosphere, 300° C./hr), of 0.0125 or higher but 0.0160 or lower.

10) The powder for a translucent zirconia sintered body according to 8) above which preferably is a powder containing 2-4 mol % yttria as a stabilizer, containing less than 0.1 wt % alumina, and having a rate of sintering shrinkage (Δρ/ΔT; g/cm$^3$·° C.), in a relative-density range of 70% to 90% in normal-pressure sintering (in the atmosphere, 300° C./hr), of 0.0125 or higher but 0.0160 or lower.

11) The powder for a translucent zirconia sintered body according to 8) above which preferably is a powder containing 2-4 mol % yttria as a stabilizer, containing no alumina (alumina content, 0 wt %), and having a rate of sintering shrinkage (Δρ/ΔT; g/cm$^3$·° C.), in a relative-density range of 70% to 90% in normal-pressure sintering (in the atmosphere, 300° C./hr), of 0.0120 or higher but 0.0135 or lower.

12) A process for producing a translucent zirconia sintered body, characterized by molding the zirconia powder according to any one of 8) to 11) above and then sintering the resultant green body at 1,350-1,450° C. at normal pressure.

13) A dental material comprising the sintered body according to any one of 1) to 7) above.

14) The dental material according to 13) above which preferably is a denture and/or a denture mill blank.

15) The dental material according to 13) above which preferably is an orthodontic bracket.

It has been known that fine alumina (sol or the like) is used for a high-density zirconia sintered body. However, such zirconia sintered bodies have been limited to ones in which fine alumina has been added in an amount exceeding 0.2 wt % in order to improve the properties required of the sintered bodies. None of such zirconia sintered bodies having a high content of alumina, which is a different kind of component, has sufficient translucency due to the influences of refraction, scattering, etc. of light, even when the sintered bodies have a high density. The invention provides a sintered body which has an alumina content of 0.2 wt % or lower or contains no alumina and which has excellent basic properties required of sintered bodies and further has excellent translucency.

Effects of the Invention

The translucent zirconia sintered body of the invention has a high density, high strength, and excellent translucency and is hence an excellent zirconia sintered body for use in dental applications, specifically, an excellent sintered body for use as a mill blank for a denture material or the like or as an orthodontic bracket. The powder of the invention for a translucent zirconia sintered body is a powder from which a translucent zirconia sintered body can be produced through normal-pressure sintering without using a large-scale pressure sintering apparatus, for example, one for HIP.

MODES FOR CARRYING OUT THE INVENTION

Figure 1:
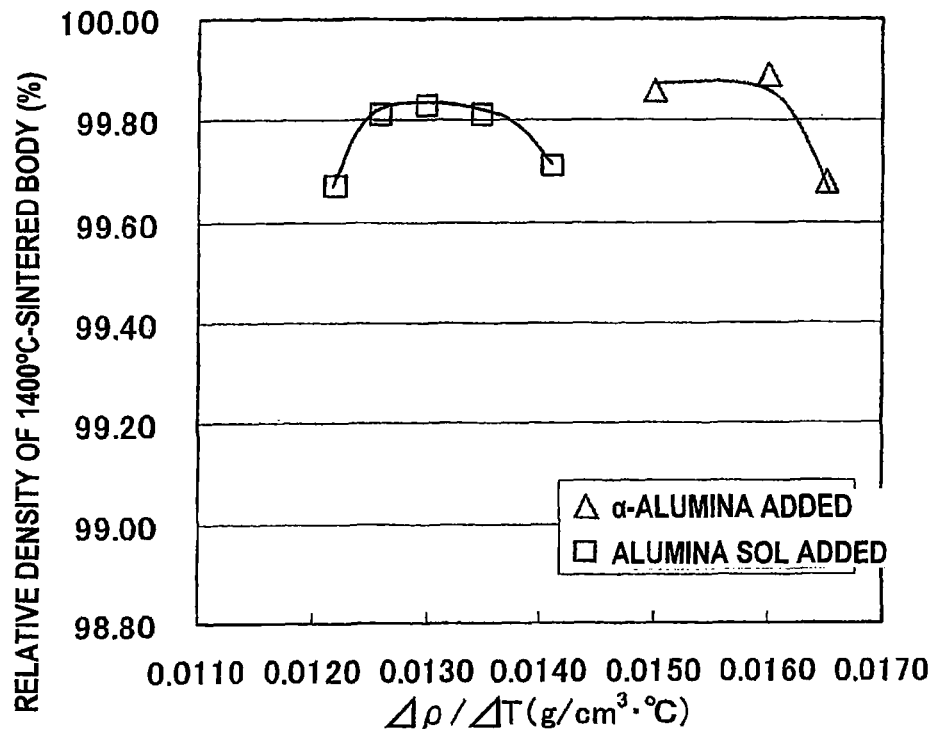
FIG. 1 is a presentation showing relationships between the rate of sintering shrinkage (Δρ/ΔT; g/cm$^3$·° C.) of zirconia containing 0.1-0.2 wt % alumina and sintered-body relative density.

The invention will be explained below in more detail.

In the invention, the "average particle diameter" of a zirconia powder means the diameter of a sphere having the same volume as a particle corresponding to the median value of a cumulative curve of particle diameter distribution expressed on a volume basis (median diameter; particle diameter corresponding to 50% of the cumulative curve). That average particle diameter is a value determined with a particle diameter distribution analyzer based on the laser diffraction method.

The term "stabilizer concentration" means the value of stabilizer/(ZrO$_2$+stabilizer) proportion given in terms of % by mole.

The term "monoclinic fraction (fm)" means the value obtained by determining the diffraction intensity of each of the (111) plane and (11-1) plane of a monoclinic phase, the (111) plane of a tetragonal phase, and the (111) plane of a cubic phase by X-ray powder diffraction (XRD) analysis and calculating the fraction using the following mathematical expression 1.

$$f_m(\%) = \frac{I_m(111) + I_m(11-1)}{I_m(111) + I_m(11-1) + I_t(111) + I_c(111)} \times 100 \quad [\text{Math. 1}]$$

(In the expression, I represents each diffracted-ray peak intensity, and the subscripts m, t, and c represent monoclinic phase, tetragonal phase, and cubic phase, respectively.)

The term "additive content" means the value of additive/(ZrO$_2$+stabilizer+additive) proportion given in terms of % by weight. Here, the amount of the additive is given in terms of oxide amount.

The "conversion" to a hydrated zirconia sol means the value obtained by subjecting a liquid containing the hydrated zirconia sol to ultrafiltration to obtain a filtrate, determining the amount of the zirconium of the unreacted materials present in the filtrate by inductively coupled plasma emission spectrometry, calculating the amount of the hydrated zirconia sol yielded, and determining the proportion of the amount of the hydrated zirconia sol to the feed amount of the starting materials.

The term "relative density" means the value obtained by measuring an actual density $\rho$ by the Archimedes method, determining a theoretical density $\rho_0$ using the following equation (2), and converting these density values to the proportion $(\rho/\rho_0) \times 100(\%)$. In equation (2), the theoretical density of alumina and the theoretical density of zirconia containing 3 mol % yttria were taken as 3.987 (g/cm$^3$) and 6.0956 (g/cm$^3$), respectively.

$$\rho_0 = 100/[(X/3.987)+(100-X)/6.0956] \quad (2)$$

{X is alumina content (% by weight).}

The translucent zirconia sintered body of the invention is explained first.

The translucent zirconia sintered body of the invention contains 2-4 mol % yttria as a stabilizer. In the case where the content of the stabilizer is lower than 2 mol %, the resultant sintered body has reduced strength. Furthermore, crystalline phases become unstable, making it difficult to produce a sintered body. In the case where the content thereof exceeds 4 mol %, the resultant sintered body has considerably reduced strength. Yttria concentrations in the sintered body which are suitable for high strength are 2.5-3 mol %, and yttria concentrations in the sintered body which are suitable for total light transmittance are 3-4 mol %.

Furthermore, the translucent zirconia sintered body of the invention has an alumina content of 0.2 wt % or lower. Alumina contents exceeding 0.2 wt % result in too high a rate of sintering and hence in the formation of many voids during sintering. The resultant sintered body has a relative density lower than 99.8% and further has poor translucency.

In the case where the translucent zirconia sintered body of the invention contains alumina, it is preferred that at least 0.005 wt % alumina should be contained. However, the translucent zirconia sintered body need not always contain alumina.

The translucent zirconia sintered body of the invention satisfies the composition described above and has a relative density of 99.8% or higher, and this enables the sintered body to satisfy a total light transmittance, as measured at a thickness of 1.0 mm, of 35% or higher.

The translucent zirconia sintered body of the invention is obtained through normal-pressure sintering without using pressure sintering such as HIP. This translucent zirconia sintered body has a total light transmittance, as measured at a thickness of 1.0 mm, of at least 35% or higher, preferably 37% or higher, more preferably 40% or higher, and may have high translucency with a total light transmittance reaching 45%.

It is preferred that the translucent zirconia sintered body of the invention should further have a crystal grain diameter of 0.20-0.45 μm. In the case where the crystal grain diameter thereof is smaller than 0.20 μm, there are many fine voids between the grains and within the grains and, hence, the relative density does not reach 99.8%. Crystal grain diameters thereof exceeding 0.45 μm are unsuitable because hydrothermal deterioration of this sintered body proceeds considerably and the sintered body thereby breaks.

It is preferred that the translucent zirconia sintered body of the invention should have a monoclinic fraction of 30% or lower after 24-hour immersion in 140° C. hot water. Monoclinic fractions exceeding 30% are unsuitable because hydrothermal deterioration of this sintered body proceeds considerably and the sintered body thereby breaks. In the case where the translucent zirconia sintered body of the invention has an alumina content lower than 0.1 wt % or contains no alumina, it is especially preferred that the monoclinic fraction should be 20% or lower, in particular, 10% or lower.

It is preferred that the translucent zirconia sintered body of the invention should have a three-point bending strength of 1,000 MPa or higher. The three-point bending strength thereof is preferably 1,100 MPa or higher, especially 1,200 MPa or higher, more preferably 1,300 MPa or higher. In the case where the alumina addition amount is 0.1 wt % or more, it is especially preferred that the three-point bending strength thereof should be 1,400 MPa or higher.

The zirconia powder of the invention for a translucent zirconia sintered body is explained next.

The zirconia powder of the invention for a translucent zirconia sintered body contains 2-4 mol % yttria as a stabilizer and has an alumina content of 0.2 wt % or lower.

It is preferred that the zirconia powder of the invention for a translucent zirconia sintered body should have a BET specific surface area in the range of 5-16 m$^2$/g. In particular, it is preferred that when the powder has an alumina content of 0.2 wt % or lower, the BET specific surface area thereof should be 5-15 m$^2$/g, and that when the powder contains no alumina, the BET specific surface area thereof should be 10-16 m$^2$/g. In the case where the BET specific surface area of the zirconia powder is smaller than 5 m$^2$/g, this powder is less apt to be sintered at lower temperatures. In the case where the BET specific surface area thereof is larger than 16 m$^2$/g, this powder has a considerably weak cohesive force between particles.

It is preferred that the zirconia powder of the invention for a translucent zirconia sintered body should have an average particle diameter in the range of 0.3-0.7 μm. In particular, it is preferred that when the powder has an alumina content of 0.1-0.2 wt %, the average particle diameter thereof should be 0.3-0.7 μm, especially 0.4-0.5 μm, and that when the powder has an alumina content lower than 0.1 wt % or contains no alumina, then the average particle diameter thereof should be 0.4-0.7 μm, especially 0.5-0.6 μm. In the case where the average particle diameter of the zirconia powder is smaller than 0.3 μm, this powder is difficult to mold because the proportion of fine particles, which enhance the cohesiveness of the powder, is large. On the other hand, in the case where the average particle diameter thereof exceeds 0.7 μm, this powder is difficult to mold because the proportion of coarse particles including hard aggregates is large. In addition, such coarse particles inhibit densification and, hence, this powder has poor sinterability.

The zirconia powder of the invention for a translucent zirconia sintered body may be obtained, for example, by drying, calcining, and grinding a hydrated zirconia sol obtained by hydrolyzing an aqueous solution of a zirconium salt. Furthermore, it is preferred to obtain a hydrated zirconia sol by adding an alkali metal hydroxide and/or an alkaline earth metal hydroxide to the aqueous solution of a zirconium salt and then hydrolyzing the aqueous solution to a conversion of 98% or higher and to add yttrium as a raw material for a stabilizer to the hydrated zirconia sol and dry the mixture.

Examples of the zirconium salt to be used in producing the hydrated zirconia sol include zirconium oxychloride, zirconium nitrate, zirconium chloride, and zirconium sulfate. Besides these, a mixture of zirconium hydroxide and an acid may be used. Examples of the alkali metal hydroxide and/or alkaline earth metal hydroxide to be added to the aqueous zirconium salt solution include the hydroxides of lithium, sodium, potassium, magnesium, and calcium. It is preferred that these hydroxides should be added in the form of an aqueous solution.

The dry powder of a hydrated zirconia sol obtained above is calcined at a temperature of 1,000-1,250° C. In the case where the powder is calcined at a temperature outside the range, the zirconia powder to be obtained by grinding the calcined powder under the following grinding conditions has considerably enhanced cohesiveness or contains a larger proportion of coarse particles including hard aggregates. Because of this, the resultant powder has an average particle diameter outside the range of 0.3-0.7 µm, and a zirconia powder of the invention is not obtained. More preferred calcination temperatures are 1,050-1,150° C.

It is preferred that the calcined powder obtained above should be subsequently wet-grinding with zirconia balls having a diameter of 3 mm or smaller until the average particle diameter thereof comes to be in the range of 0.3-0.7 µm (in particular, 0.4-0.7 µm, when the powder has an alumina content lower than 0.1 wt % or contains no alumina) to thereby further regulate the sinterability thereof so as to be in the range according to the invention.

Examples of an aluminum compound to be used as an additive in the zirconia powder of the invention for a translucent zirconia sintered body include alumina, hydrated alumina, alumina sol, aluminum hydroxide, aluminum chloride, aluminum nitrate, and aluminum sulfate.

In the case of using an alumina sol, an alumina sol having an average particle diameter of 0.01-0.05 µm and a BET specific surface area of 30-150 m$^2$/g or an alumina sol having a BET specific surface area of 30-290 m$^2$/g can be used in such a manner that the sol is mixed with the zirconia powder and the mixture is sintered.

In the case of using alumina, α-alumina having an average particle diameter of 0.05-0.5 µm and a BET specific surface area of 5-50 m$^2$/g can be used.

The zirconia powder of the invention for a translucent zirconia sintered body has a rate of sintering shrinkage (Δρ/ΔT; g/cm$^3$·° C.) in a relative-density range of 70% to 90% in normal-pressure sintering (in the atmosphere, 300° C./hr) (hereinafter referred to as "rate of sintering shrinkage") of 0.0120 or higher but 0.0160 or lower.

The zirconia powder of the invention, when compacted by ordinary press molding (isostatic pressing (CIP) conducted according to need), gives a green body having a relative density of about 50±5%. When this green body is heated in the atmosphere, sintering shrinkage begins at a temperature not lower than the calcination temperature, in particular at around 1,100° C. The rate of sintering shrinkage is constant in the relative-density range of 70% to 90%, and the rate of shrinkage gradually decreases after the relative density has exceeded 90%. Around 100%, the body comes not to shrink even when the temperature is elevated further.

After the zirconia powder has been molded (molded with a mold and then subjected to CIP (pressure, 2 t/cm$^2$)), the rate of sintering shrinkage can be measured with a general thermodilatometer (DL 9700, manufactured by ULVAC-RIKO, Inc.). The rate of sintering shrinkage in the invention is a value measured when the relative density is 70% or higher and, hence, is not influenced by unevenness of the initial body density (relative density, around 50%). Furthermore, in the relative-density range of 70% to 90%, the rate of sintering shrinkage is constant and, hence, the rate of shrinkage is given as the linear function of temperature and relative density. Consequently, the accurate rate of shrinkage can be easily determined without necessitating a special calculation for approximation.

In the case where the rate of sintering shrinkage of the zirconia powder of the invention for a translucent zirconia sintered body is outside the range, it is difficult to obtain a sintered body having a relative density of 99.8% or higher and high translucency.

The zirconia powder of the invention gives, through normal-pressure sintering, a sintered body having high translucency, and a sintered body having high translucency is obtained therefrom without necessitating pressure sintering such as HIP. Furthermore, it is preferred that the zirconia powder of the invention should have specific sinterability (rate of sintering shrinkage) suitable for the properties of the alumina used. This does not mean that the higher the rate of sintering shrinkage, the more the powder of the invention is preferred. In the case where the powder has a rate of sintering shrinkage outside the range suitable for the properties of the alumina, it is difficult to obtain a sintered body having high translucency through normal-pressure sintering.

The rate of sintering shrinkage used in the invention varies as the rate of heating changes. However, when the rate of heating is fixed, the rate of sintering shrinkage has a constant value, which is inherent in the powder.

In the case where the powder of the invention contains alumina, the rate of sintering shrinkage thereof is preferably 0.0125 or higher but 0.0160 or lower.

When the powder of the invention contains alumina and the alumina used has an average particle diameter of 0.01 µm or larger but 0.05 µm or smaller, then the rate of sintering shrinkage thereof is preferably 0.0125 or higher but 0.0135 or lower. In the case where the rate of sintering shrinkage thereof is outside the range, a zirconia sintered body having high translucency is not obtained through normal-pressure sintering, especially through normal-pressure sintering conducted at a sintering temperature of 1,450° C. or lower, in particular, 1,400° C. or lower.

When the powder of the invention contains alumina and the alumina used has an average particle diameter larger than 0.05 µm but not larger than 0.5 µm, then the rate of sintering shrinkage is preferably higher than 0.0135 but not higher than 0.0160. In the case where the rate of sintering shrinkage thereof exceeds 0.0160, a sintered body having high translucency is not obtained through normal-pressure sintering, especially through normal-pressure sintering conducted at a sintering temperature of 1,450° C. or lower, in particular, 1,400° C. or lower. On the other hand, in the case where alumina having an average particle diameter larger than 0.05 µm but not larger than 0.5 µm is used in a composition according to the invention, it is difficult to prepare a powder having a rate of sintering shrinkage lower than 0.0135.

In the case where the powder of the invention contains no alumina, it is preferred that the rate of sintering shrinkage of this powder of the invention should be 0.0120 or higher but 0.0135 or lower, in particular, 0.0125 or higher but 0.0135 or lower.

It is preferred that the zirconia powder of the invention for a translucent zirconia sintered body should be an atomized molding granular powder. It is especially preferred to use an atomized granular powder containing an organic binder besides yttria as a stabilizer and alumina as an additive.

A zirconia powder is slurried and spray-dried to obtain zirconia granules. The zirconia granules thus obtained show enhanced flowability when used for forming a green body and give a sintered body which is less apt to have voids formed therein. It is preferred that the granules should have a particle diameter of 30-80 µm and a bulk density of 1.10-1.40 g/cm$^3$.

In the case where a binder is used in the granules, examples of the binder include binders in general use, such as poly(vinyl alcohol), poly(vinyl butyrate), waxes, and acrylics. Preferred of these are acrylic binders having carboxyl groups or a derivative thereof (for example, a salt, in particular, ammonium salt or the like) in the molecule. Examples of the acrylic binders include poly(acrylic acid), poly(methacrylic acid), acrylic acid copolymers, methacrylic acid copolymers, and derivatives thereof. The amount of the binder to be added is preferably 0.5-10% by weight, especially preferably 1-5% by weight, based on the ceramic powder contained in the ceramic-powder slurry.

It is preferred that the translucent zirconia sintered body of the invention should be produced by molding a zirconia powder containing 2-4 mol % yttria as a stabilizer and 0.2 wt % or less alumina sol having a particle diameter of 0.01-0.05 μm as an additive and then sintering the body at normal pressure and a sintering temperature of 1,350-1,450° C., in particular, 1,400° C. or lower, at a heating rate of 100° C./hr or lower.

In the case where a sintering temperature lower than 1,350° C. is used, a relative density of 99.8% is not reached. On the other hand, in the case where a sintering temperature exceeding 1,450° C. is used, hydrothermal deterioration of the sintered body proceeds considerably and the sintered body is hence apt to break.

Although the translucent zirconia sintered body of the invention is obtained through normal-pressure sintering, the atmosphere for sintering is not particularly limited unless the atmosphere is a reducing atmosphere. Sintering in an oxygen atmosphere or in the air is preferred. It is especially preferred to sinter the body in the air.

EXAMPLES

The invention will be explained below in detail by reference to Examples, but the invention should not be construed as being limited to the Examples.

In the Examples and Comparative Examples, the average particle diameter of each fine zirconia powder was determined with a Microtrac particle size distribution analyzer (Type 9320-HRA, manufactured by Honeywell Inc.). With respect to pretreatment conditions for each sample, the powder was suspended in distilled water and dispersed therein for 3 minutes using an ultrasonic homogenizer (Type US-150T, manufactured by Nihonseiki Kaisha Ltd.). The monoclinic fraction, which is determined through XRD analysis, was calculated using mathematical expression 1 (in each example, no cubic crystals were contained). The average particle diameter of zirconia granules was determined by a sieve analysis test method.

A raw-material powder was preformed with a mold press at a pressure of 700 kgf/cm². The preformed object obtained was subjected to cold isostatic pressing (CIP) using a rubber mold at a pressure of 2 t/cm² to obtain a green body. The green body obtained was sintered at a given set temperature (holding period, 2 hours). The average crystal grain diameter of the zirconia sintered body was determined by mirror-polishing the sintered body, heat-etching the minor-polished sintered body, and calculating the average diameter by a planimetric method using a field emission scanning electron microscope (FESEM) (Type JSM-T220, manufactured by JEOL Ltd.). The density of the sintered body was determined by the Archimedes method.

The total light transmittance of the sintered body was measured with a turbidimeter (Type NDH 2000, manufactured by Nippon Denshoku Kogyo K.K.) using illuminant D65 in accordance with JIS K7361. The sample used was a disk-shaped sample having a thickness of 1 mm obtained by polishing both sides of the sintered body. The strength of the sintered body was evaluated by the three-point bending test method.

In a hydrothermal durability test, the sintered body was immersed in 140° C. hot water for 24 hours and the proportion of the resultant monoclinic phase (monoclinic fraction) was determined to thereby evaluate hydrothermal durability. The monoclinic fraction was determined by subjecting the sintered body which had undergone the immersion treatment to XRD analysis and calculating the proportion using mathematical expression 1, which has been described above, in the same manner as for the monoclinic fraction of the fine zirconia powder.

Example 1

An aqueous solution of potassium hydroxide was added to a 0.4 mol/L aqueous solution of zirconium oxychloride to prepare an aqueous solution having a molar concentration ratio [OH]/[Zr] of 0.02. While this solution was being stirred in a flask equipped with a reflux condenser, a hydrolysis reaction was conducted at the boiling temperature for 350 hours. The conversion to the hydrated zirconia sol obtained was 99%. Distilled water was added to this hydrated zirconia sol to prepare a solution having a concentration of 0.3 mol/L in terms of zirconia concentration. This solution was used as a starting solution to conduct a hydrolysis reaction at the boiling temperature for 200 hours while intermittently discharging 5% by volume of the solution from the reaction vessel and feeding an aqueous zirconium oxychloride solution to which 0.3 mol/L aqueous sodium hydroxide solution had been added ([OH]/[Zr]=0.02). This aqueous zirconium oxychloride solution was fed at intervals of 30 minutes in the same amount as the discharge amount so that the volume of the solution in the reaction vessel was kept constant. In the hydrated zirconia sol discharged from the reaction vessel, the conversion to the sol was 99%.

Yttrium chloride was added to the hydrated zirconia sol so as to result in an yttria concentration of 3% by mole, and the resultant mixture was dried and calcined at a temperature of 1,140° C. for 2 hours. The calcined powder obtained was washed with water. Thereafter, an alumina sol having a particle diameter of 0.015 μm was added thereto in an amount of 0.10% by weight in terms of alumina content, and distilled water was further added to obtain a slurry having a zirconia concentration of 45% by weight. This slurry was treated with a vibration mill for 24 hours using zirconia balls having a diameter of 2 mm Thus, a zirconia powder was obtained.

The values of $Al_2O_3$ content, BET specific surface area, average particle diameter, and monoclinic fraction of the zirconia powder obtained are shown in Table 1.

The zirconia powder obtained was dispersed in water to obtain a zirconia slurry having a slurry concentration of 50%. A thickener was added to the slurry to regulate the viscosity thereof, and this slurry was then granulated by spraying. The zirconia granules obtained had an average particle diameter of 50 μm and a bulk density of 1.21 g/cm³.

Subsequently, the zirconia granules obtained above were press-molded by CIP (pressure, 2 t/cm²) and sintered under the conditions of 1,450° C. The sintering temperature for the sintered body obtained and the properties of the sintered body, i.e., density, bending strength, crystal grain diameter, and monoclinic fraction after the hydrothermal durability test, are shown in Table 2.

The sintered body obtained had a total light transmittance of 37% and was ascertained to be a sintered body having excellent translucency. The monoclinic fraction after the hydrothermal durability test was 21%, and the sintered body was thus ascertained to be less apt to deteriorate.

Example 2

A zirconia powder was obtained in the same manner as in Example 1, except that the alumina sol was added in an amount of 0.12% by weight in terms of alumina content. The properties of the zirconia powder obtained are shown in Table 1. Thereafter, the zirconia powder obtained was dispersed in water to obtain a zirconia slurry having a slurry concentration of 50%. An acrylic binder and poly(vinyl alcohol) were added to the slurry in an amount of 3 wt % based on the zirconia contained in the zirconia slurry, and a thickener was added to regulate the viscosity. Thereafter, the slurry was granulated by spraying to produce zirconia granules. The zirconia granules obtained had an average particle diameter of 45 μm and a bulk density of 1.20 g/cm$^3$.

Subsequently, the zirconia granules obtained above were press-molded by CIP (pressure, 2 t/cm$^2$) and sintered under the conditions of 1,450° C.

The sintering temperature for the sintered body obtained and the properties of the sintered body, i.e., density, bending strength, crystal grain diameter, and monoclinic fraction after the hydrothermal durability test, are shown in Table 2.

The sintered body obtained had a total light transmittance of 35% and was ascertained to be a sintered body having excellent translucency. The monoclinic fraction after the deterioration test was 20%, and the sintered body was thus ascertained to be less apt to deteriorate.

Example 3

A zirconia powder was obtained under the same conditions as in Example 1, except that the alumina sol was added in an amount of 0.17% by weight in terms of alumina content. The properties of the zirconia powder obtained are shown in Table 1. This zirconia powder was used to obtain zirconia granules by the same method as in Example 2. The zirconia granules obtained had an average particle diameter of 40 μm and a bulk density of 1.18 g/cm$^3$.

Subsequently, the zirconia granules obtained above were press-molded and sintered under the conditions of 1,400° C. The sintering temperature for the sintered body obtained and the properties of the sintered body, i.e., density, bending strength, crystal grain diameter, and monoclinic fraction after the deterioration test, are shown in Table 2.

The sintered body obtained had a total light transmittance of 39% and was ascertained to be a sintered body having excellent translucency. The monoclinic fraction after the deterioration test was 28%, and the sintered body was thus ascertained to be less apt to deteriorate.

Example 4

A zirconia sintered body was obtained by the same method as in Example 3, except that the sintering temperature for the zirconia granules was changed to 1,350° C. and that during the sintering, the green body was heated at a low heating rate of 50° C./hr, although heating at 100° C./hr is usually employed. The sintering temperature for the sintered body obtained and the properties of the sintered body, i.e., density, bending strength, crystal grain diameter, and monoclinic fraction after the hydrothermal durability test, are shown in Table 2.

The sintered body obtained had a total light transmittance of 38% and was ascertained to be a sintered body having excellent translucency. The monoclinic fraction after the deterioration test was 5%, and the sintered body was thus ascertained to be less apt to deteriorate.

Example 5

A zirconia powder was obtained by the same method as in Example 3, except that the calcination temperature in zirconia powder production was changed to 1,220° C. The properties of the fine zirconia powder obtained are shown in Table 1.

This fine zirconia powder was used to obtain zirconia granules by the same method as in Example 2. The zirconia granules obtained had an average particle diameter of 40 μm and a bulk density of 1.12 g/cm$^3$.

Subsequently, the zirconia granules obtained above were press-molded and sintered under the conditions of 1,400° C. During the sintering, however, the green body was heated at a low heating rate of 50° C./hr, although heating at 100° C./hr is usually employed. The sintering temperature for the sintered body obtained and the properties of the sintered body, i.e., density, bending strength, crystal grain diameter, and monoclinic fraction after the hydrothermal durability test, are shown in Table 2.

The sintered body obtained had a total light transmittance of 39% and was ascertained to be a sintered body having excellent translucency. The monoclinic fraction after the hydrothermal durability test was 27%, and the sintered body was thus ascertained to be less apt to deteriorate.

Example 6

A zirconia powder was obtained by the same method as in Example 3, except that the calcination temperature in zirconia powder production was changed to 1,080° C. The properties of the zirconia powder obtained are shown in Table 1.

This zirconia powder was used to obtain zirconia granules by the same method as in Example 2. The zirconia granules obtained had an average particle diameter of 42 μm and a bulk density of 1.23 g/cm$^3$.

Subsequently, the zirconia granules obtained above were press-molded and sintered under the conditions of 1,400° C. During the sintering, however, the green body was heated at a low heating rate of 50° C./hr, although heating at 100° C./hr is usually employed. The sintering temperature for the sintered body obtained and the properties of the sintered body, i.e., density, bending strength, crystal grain diameter, and monoclinic fraction after the hydrothermal durability test, are shown in Table 2.

The sintered body obtained had a total light transmittance of 38% and was ascertained to be a sintered body having excellent translucency. The monoclinic fraction after the hydrothermal durability test was 29%, and the sintered body was thus ascertained to be less apt to deteriorate.

Comparative Example 1

A zirconia powder was obtained in the same manner as in Example 1, except that the alumina sol was added in an amount of 0.075% by weight in terms of alumina content. This zirconia powder was used to obtain zirconia granules by the same method as in Example 1. The properties of the zirconia powder obtained are shown in Table 1.

Subsequently, the zirconia granules obtained above were press-molded by CIP (pressure, 2 t/cm$^2$) and sintered under the conditions of 1,450° C. The sintering temperature for the sintered body obtained and the properties of the sintered body, i.e., density, bending strength, crystal grain diameter, and monoclinic fraction after the hydrothermal durability test, are shown in Table 2.

The sintered body obtained had a monoclinic fraction after the hydrothermal durability test of 10%, and was ascertained to be a sintered body which was less apt to deteriorate. However, the total light transmittance thereof was as low as 29%, and this sintered body was found to have poor translucency.

Comparative Example 2

A zirconia powder was obtained under the same conditions as in Example 1, except that the alumina content in Example 1 was changed to 0.25% by weight using an alumina powder and that the griding time was changed to 8 hours. This zirconia powder was used to obtain zirconia granules by the same method as in Example 2. The properties of the zirconia powder obtained are shown in Table 1.

Subsequently, the zirconia granules obtained above were press-molded by CIP (pressure, 2 t/cm$^2$) and sintered under the conditions of 1,500° C. The sintering temperature for the sintered body obtained and the properties of the sintered body, i.e., density, bending strength, crystal grain diameter, and monoclinic fraction after the hydrothermal durability test, are shown in Table 2.

The sintered body obtained had a monoclinic fraction after the hydrothermal durability test of 50%, and was ascertained to be a sintered body which was apt to deteriorate and had poor reliability. Furthermore, the total light transmittance thereof was as low as 32%, and this sintered body was found to have poor translucency.

Comparative Example 3

A zirconia powder was obtained under the same conditions as in Example 1, except that the calcination temperature in Example 1 was changed to 900° C., the alumina content was changed to 0.25% by weight using an alumina powder, and treatment with the vibration mill was conducted for 8 hours. This zirconia powder was used to obtain zirconia granules by the same method as in Example 2.

The properties of the zirconia powder obtained are shown in Table 1.

Subsequently, the zirconia granules obtained above were press-molded and sintered under the conditions of 1,350° C. The sintering temperature for the sintered body obtained and the properties of the sintered body, i.e., density, bending strength, crystal grain diameter, and monoclinic fraction after the hydrothermal durability test, are shown in Table 2.

The sintered body obtained had a monoclinic fraction after the hydrothermal durability test of 5%, and was ascertained to be a sintered body which was less apt to deteriorate. However, the total light transmittance of this sintered body was found to be as extremely low as 18%.

TABLE 1

| | BET specific surface area (m$^2$/g) | Average particle diameter (μm) | Proportion of monoclinic phase (%) |
|---|---|---|---|
| Example 1 | 8.2 | 0.49 | 27 |
| Example 2 | 8.0 | 0.47 | 28 |
| Example 3 | 8.0 | 0.48 | 28 |
| Example 4 | 8.0 | 0.48 | 28 |
| Example 5 | 7.1 | 0.50 | 28 |
| Example 6 | 9.0 | 0.45 | 27 |
| Comparative Example 1 | 8.0 | 0.47 | 28 |
| Comparative Example 2 | 7.2 | 0.64 | 19 |
| Comparative Example 3 | 17.8 | 0.35 | 25 |

TABLE 2

| | Sintering temperature (° C.) | Density of sintered body (%) | Bending strength (MPa) | Crystal grain diameter (μm) | Proportion of monoclinic phase (%) | Total light transmittance (%) |
|---|---|---|---|---|---|---|
| Example 1 | 1450 | 99.8 | 1200 | 0.43 | 21 | 37 |
| Example 2 | 1450 | 99.8 | 1400 | 0.44 | 20 | 35 |
| Example 3 | 1400 | 99.8 | 1400 | 0.35 | 28 | 39 |
| Example 4 | 1350 | 99.8 | 1300 | 0.28 | 5 | 38 |
| Example 5 | 1400 | 99.8 | 1400 | 0.36 | 27 | 39 |
| Example 6 | 1400 | 99.8 | 1400 | 0.34 | 29 | 38 |
| Comparative Example 1 | 1450 | 99.6 | 1300 | 0.42 | 10 | 29 |
| Comparative Example 2 | 1500 | 99.7 | 1400 | 0.55 | 50 | 32 |
| Comparative Example 3 | 1350 | 99.4 | 1200 | 0.28 | 5 | 18 |

Examples 7 to 10 and Comparative Examples 4 to 7

Yttrium chloride was added to a hydrated zirconia sol obtained by a hydrolysis reaction, in such an amount as to result in an yttria concentration of 3% by mole. The resultant mixture was dried. Thereafter, the same alumina sol as that used in Examples 1 to 6 and an α-alumina powder having an average particle diameter of 0.3 μm were used to prepare zirconia powders having a BET surface area of 10-15 m$^2$/g.

The powders obtained were press-molded by CIP (pressure, 2 t/cm$^2$) and sintered under the conditions of 1,400° C. Furthermore, green bodies obtained by CIP molding in the same manner were examined for the rate of sintering shrinkage using a heat shrinkage meter (DL 9700, manufactured by ULVAC-RIKO, Inc.).

In Table 3 are shown the content of Al$_2$O$_3$ (particle diameter), BET specific surface area, and rate of sintering shrinkage of each zirconia powder and the density of the sintered body obtained therefrom through atmospheric sintering at normal pressure and 1,400° C. using a heating rate of 100° C./hr.

In the case where the alumina had an average particle diameter of 0.01 μm or larger but less than 0.05 μm, a translucent zirconia sintered body having a relative density of 99.8% or higher was obtained when the rate of sintering shrinkage was 0.0125 or higher but 0.0135 or lower. In the case where the alumina had an average particle diameter larger than 0.05 μm but not larger than 0.5 μm, a translucent zirconia sintered body having a relative density of 99.8% or higher was obtained when the rate of sintering shrinkage was higher than 0.0135 but not higher than 0.0160.

Figure 2:
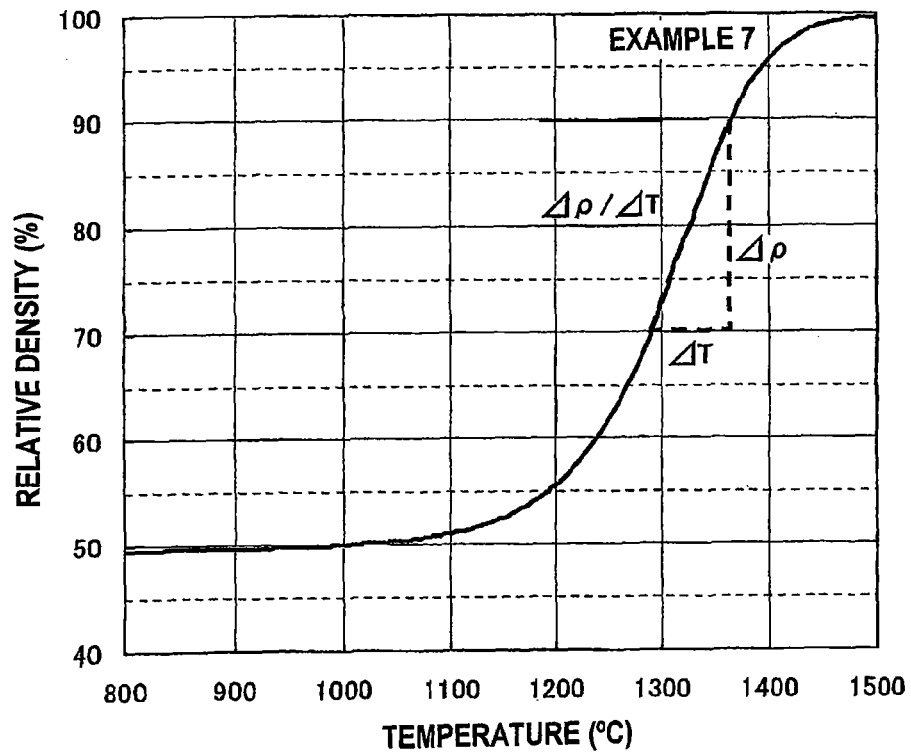
FIG. 2 is a presentation showing an example of heat shrinkage curves obtained in the atmospheric normal-pressure sintering of a zirconia powder (heating rate, 300° C./hr) (Example 7).

Relationships between the rate of sintering shrinkage and the relative density of the sintered body are shown in FIG. 1. A heat shrinkage curve in the sintering in Example 7 is shown in FIG. 2.

TABLE 3

| No. | Particle diameter of Al$_2$O$_3$ (μm) | Content of Al$_2$O$_3$ (wt %) | BET specific surface area (m$^2$/g) | Rate of sintering shrinkage (Δρ/ΔT; g/cm$^3$ · ° C.) | Relative density, 1400° C. sintering (%) |
|---|---|---|---|---|---|
| Comparative Example 4 | 0.3 (α-alumina) | 0.1 | 13.6 | 0.0165 | 99.68 |
| Example 7 | | | 11.6 | 0.0160 | 99.89 |
| Example 8 | | | 10.6 | 0.0150 | 99.84 |
| Comparative Example 6 | | 0.05 | 11.8 | 0.0129 | 99.72 |
| Comparative Example 5 | 0.02 (alumina sol) | 0.1 | 10.6 | 0.0122 | 99.67 |
| Example 9 | | 0.15 | 10.8 | 0.0130 | 99.83 |
| Example 10 | | 0.1 | 11.6 | 0.0135 | 99.81 |
| Comparative Example 7 | | | 13.9 | 0.0141 | 99.71 |

When the content of alumina was 0.1-0.2 wt %, only the sintered bodies having a relative density of 99.8% or higher had translucency with a total light transmittance of 35% or higher. Consequently, a relative density of 99.8% or higher is indispensable to the attainment of a transmittance of 35% or higher.

Examples 11 to 28 and Comparative Examples 8 to 12

Yttrium chloride was added to a hydrated zirconia sol obtained by hydrolyzing zirconium oxychloride, in such an amount as to result in an yttria concentration of 3% by mole. The resultant mixture was dried and calcined for 1-10 hours at a calcination temperature of 1,000-1,200° C.

The calcined powders obtained were washed with water. Thereafter, an alumina sol having an average particle diameter of 0.015 μm or α-alumina having an average particle diameter of 0.3 μm was added to each calcined powder in an amount of 0.005-0.075 wt % in terms of alumina content, and distilled water was further added to obtain a slurry having a zirconia concentration of 45% by weight. This slurry was subjected to a grinding treatment with a vibration mill for 24-36 hours using zirconia balls having a diameter of 3 mm. Thus, zirconia powders were obtained.

The powders obtained were press-molded by CIP (pressure, 2 t/cm$^2$) and sintered under the conditions of 1,400° C. or 1,450° C. Furthermore, green bodies obtained by CIP molding in the same manner were examined for the rate of sintering shrinkage using a heat shrinkage meter (DL 9700, manufactured by ULVAC-RIKO, Inc.).

In Table 4 are shown the content of Al$_2$O$_3$ (particle diameter), BET specific surface area, and rate of sintering shrinkage of each zirconia powder, the density of the sintered body obtained therefrom through atmospheric sintering at normal pressure, 1,400° C., and 100° C./hr, and the average crystal grain diameter, total light transmittance, bending strength, and monoclinic fraction after hydrothermal deterioration.

BET specific surface area and the rate of sintering shrinkage were varied by changing calcination conditions. As a result, in the case where the alumina had an average particle diameter of 0.01 μm or larger but less than 0.05 μm, a translucent zirconia sintered body having a relative density of 99.8% or higher was obtained when the rate of sintering shrinkage was 0.0125 or higher but 0.0140 or lower. On the other hand, in the case where the alumina had an average particle diameter larger than 0.05 μm but not larger than 0.5 μm, a translucent zirconia sintered body having a relative density of 99.8% or higher was obtained when the rate of sintering shrinkage was higher than 0.0135 but not higher than 0.0160.

Figure 3:
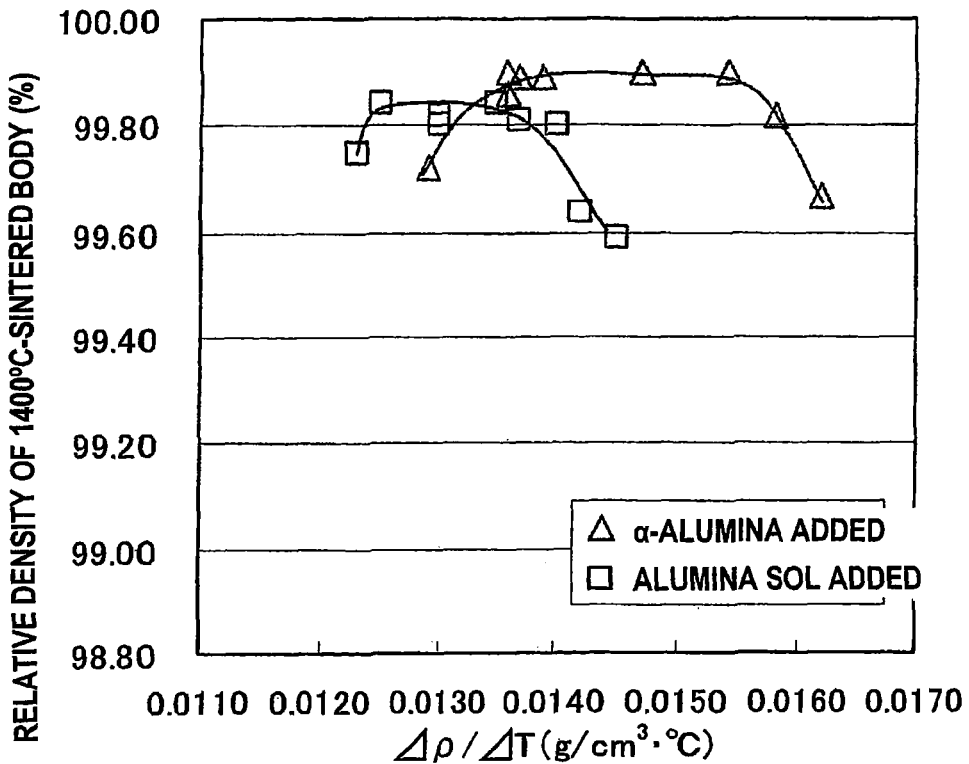
FIG. 3 is a presentation showing relationships between the rate of sintering shrinkage (Δρ/ΔT; g/cm$^3$·° C.) of zirconia containing less than 0.1 wt % alumina and sintered-body relative density.
Figure 4:
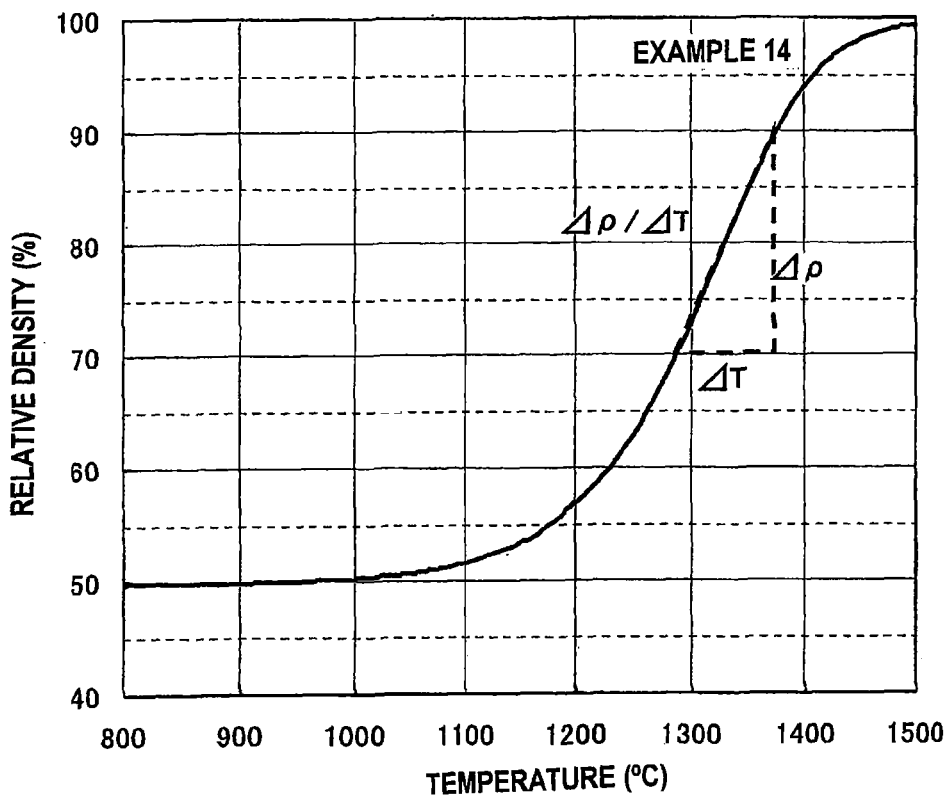
FIG. 4 is a presentation showing an example of heat shrinkage curves obtained in the atmospheric normal-pressure sintering of a zirconia powder (heating rate, 300° C./hr) (Example 14).

Relationships between the rate of sintering shrinkage and sinter density are shown in FIG. 3. A heat shrinkage curve in Example 14 is shown in FIG. 4.

TABLE 4

| No. | Particle diameter of Al$_2$O$_3$ (μm) | Content of Al$_2$O$_3$ (wt %) | BET specific surface area (m$^2$/g) | Rate of sintering shrinkage (Δρ/ΔT; g/cm$^3$ · ° C.) | Relative density (%) | Average crystal grain diameter (μm) | Total light transmittance (%) | Bending strength (MPa) | Proportion of monoclinic phase after deterioration test (%) | Remarks |
|---|---|---|---|---|---|---|---|---|---|---|
| Ex. 11 | 0.3 (α-alumina) | 0.005 | 14.2 | 0.0136 | 99.90 | 0.31 | 38.0 | 1260 | 10 | sintering, 1400° C. |
| Ex. 12 | | 0.01 | 14.8 | 0.0136 | 99.86 | 0.32 | 37.9 | 1230 | 8 | sintering, 1400° C. |
| Ex. 13 | | 0.02 | 12.0 | 0.0139 | 99.89 | 0.31 | 38.8 | — | 8 | sintering, 1400° C. |
| Comp. Ex. 8 | | 0.05 | 11.1 | 0.0129 | 99.72 | 0.32 | 32.0 | — | ≤5 | sintering, 1400° C. |
| Ex. 14 | | 0.05 | 11.9 | 0.0137 | 99.89 | 0.31 | 38.9 | — | ≤5 | sintering, 1400° C. |
| Ex. 15 | | 0.05 | 13.5 | 0.0147 | 99.90 | 0.31 | 40.0 | 1280 | ≤5 | sintering, 1400° C. |
| Ex. 16 | | 0.05 | 13.8 | 0.0158 | 99.82 | 0.31 | 36.2 | — | ≤5 | sintering, 1400° C. |
| Comp. Ex. 9 | | 0.05 | 15.6 | 0.0162 | 99.67 | 0.32 | 24.5 | — | ≤5 | sintering, 1400° C. |
| Ex. 17 | | 0.05 | 13.3 | — | 99.90 | 0.31 | 40.6 | 1160 | 5 | sintering, 1400° C. |

TABLE 4-continued

| No. | Particle diameter of $Al_2O_3$ (μm) | Content of $Al_2O_3$ (wt %) | BET specific surface area (m²/g) | Rate of sintering shrinkage (Δρ/ΔT; g/cm³·°C.) | Relative density (%) | Average crystal grain diameter (μm) | Total light transmittance (%) | Bending strength (MPa) | Proportion of monoclinic phase after deterioration test (%) | Remarks |
|---|---|---|---|---|---|---|---|---|---|---|
| Ex. 18 | | 0.05 | 12.8 | — | 99.89 | 0.42 | 41.2 | — | — | sintering, 1450° C. |
| Ex. 19 | | 0.05 | 13.3 | — | 99.92 | 0.43 | 41.4 | — | 83 | sintering, 1450° C. |
| Ex. 20 | | 0.05 | 12.1 | — | 99.90 | 0.42 | 40.2 | — | — | sintering, 1450° C. |
| Ex. 21 | | 0.05 | 12.1 | — | 99.92 | 0.43 | 40.4 | — | 81 | sintering, 1450° C. |
| Ex. 22 | | 0.075 | 11.1 | 0.0154 | 99.90 | 0.32 | 39.9 | 1270 | 10 | sintering, 1400° C. |
| Ex. 23 | 0.02 (alumina sol) | 0.01 | 14.5 | 0.0137 | 99.81 | 0.30 | 35.1 | — | 8 | sintering, 1400° C. |
| Ex. 24 | | 0.02 | 14.0 | 0.0140 | 99.80 | 0.31 | 35.0 | 1120 | 5 | sintering, 1400° C. |
| Comp. Ex. 10 | | 0.05 | 11.9 | 0.0123 | 99.75 | 0.32 | 30.5 | — | ≤5 | sintering, 1400° C. |
| Ex. 25 | | 0.05 | 11.2 | 0.0125 | 99.84 | 0.32 | 35.2 | — | ≤5 | sintering, 1400° C. |
| Ex. 26 | | 0.05 | 13.2 | 0.0130 | 99.80 | 0.32 | 35.0 | 1180 | ≤5 | sintering, 1400° C. |
| Ex. 27 | | 0.05 | 13.7 | 0.0135 | 99.84 | 0.31 | 35.3 | — | ≤5 | sintering, 1400° C. |
| Comp. Ex. 11 | | 0.05 | 14.7 | 0.0142 | 99.64 | 0.32 | 28.1 | 980 | ≤5 | sintering, 1400° C. |
| Comp. Ex. 12 | | 0.05 | 15.6 | 0.0156 | 99.59 | 0.32 | 25.3 | | ≤5 | sintering, 1400° C. |
| Ex. 28 | | 0.075 | 11.6 | 0.0130 | 99.82 | 0.31 | 36.8 | 1250 | 10 | sintering, 1400° C. |

As apparent from FIG. 3, when the content of alumina is lower than 0.1 wt %, use of the alumina sol, which has a small particle diameter, results in a narrow tolerance range of the rate of sintering shrinkage at which a relative density of 99.8% or higher is attained through sintering conducted at a low temperature of 1,400° C. For incorporation in an amount smaller than 0.1 wt %, it is preferred to use alumina having a particle diameter of 0.05 μm or larger.

Examples 29 to 40 and Comparative Examples 13 to 16

Yttrium chloride was added to a hydrated zirconia sol obtained by the hydrolysis reaction of zirconium oxychloride, in such an amount as to result in an yttria concentration of 3% by mole. The resultant mixture was dried and calcined for 1-10 hours at a calcination temperature of 1,000-1,150° C. Distilled water was added to each calcined powder to obtain a slurry having a zirconia concentration of 45% by weight. This slurry was subjected to a grinding treatment with a vibration mill for 24 hours using zirconia balls having a diameter of 3 mm Thus, zirconia powders were obtained.

The powders obtained were press-molded by CIP (pressure, 2 t/cm²) and sintered under the conditions of 1,400° C. Furthermore, green bodies obtained by CIP molding in the same manner were examined for the rate of sintering shrinkage using a heat shrinkage meter (DL 9700, manufactured by ULVAC-RIKO, Inc.).

In Table 5 are shown the BET specific surface area and rate of sintering shrinkage of each zirconia powder, the density of the sintered body obtained therefrom through atmospheric sintering at normal pressure, 1,400° C., and 100° C./hr, and the average crystal grain diameter, total light transmittance, bending strength, and monoclinic fraction after hydrothermal deterioration.

BET specific surface area and the rate of sintering shrinkage were varied by changing calcination conditions. As a result, a translucent zirconia sintered body having a relative density of 99.8% or higher was obtained when the rate of sintering shrinkage was 0.0120 or higher but 0.0140 or lower.

Figure 5:
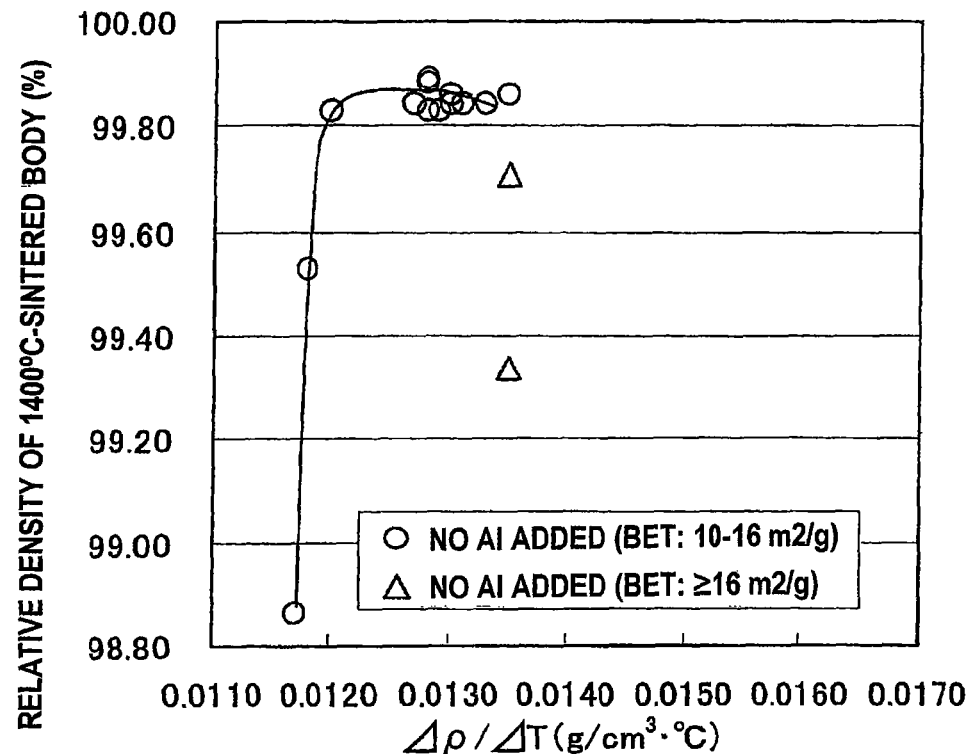
FIG. 5 is a presentation showing relationships between the rate of sintering shrinkage (Δρ/ΔT; g/cm$^3$·° C.) of zirconia containing no alumina and sintered-body relative density.
Figure 6:
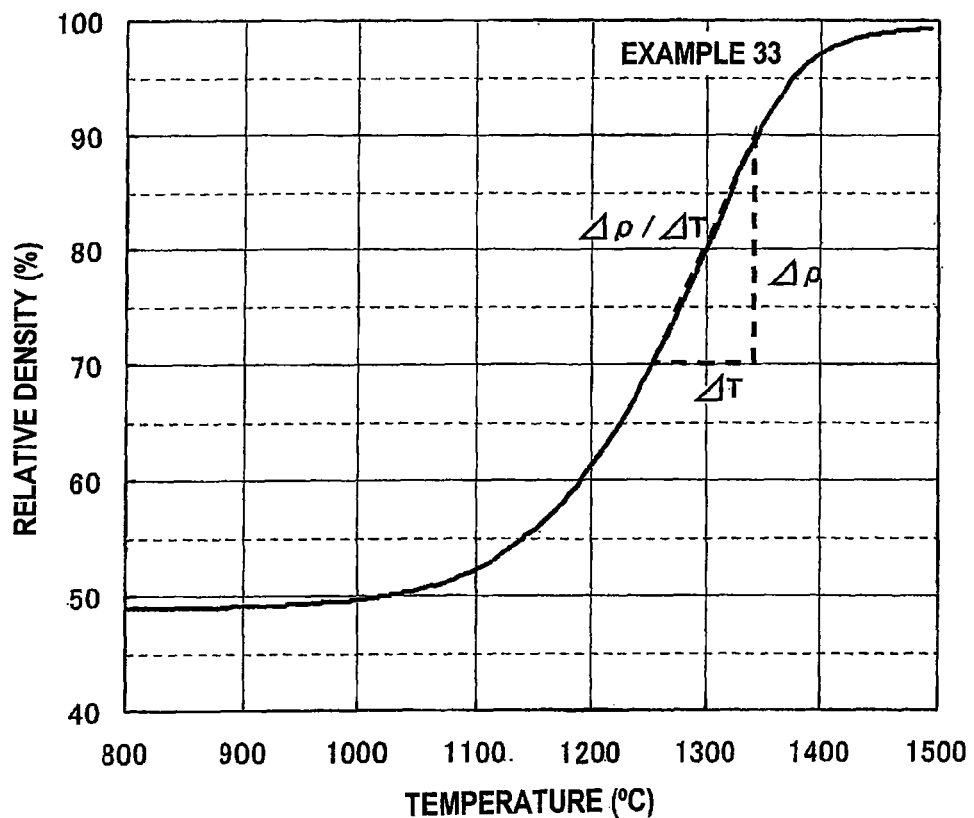
FIG. 6 is a presentation showing an example of heat shrinkage curves obtained in the atmospheric normal-pressure sintering of a zirconia powder (heating rate, 300° C./hr) (Example 33).

Relationships between the rate of sintering shrinkage and sinter density are shown in FIG. 5. A heat shrinkage curve in Example 33 is shown in FIG. 6.

TABLE 5

| No. | BET specific surface area (m²/g) | Rate of sintering shrinkage (Δρ/ΔT; g/cm³·°C.) | Relative density, 1400° C. sintering (%) | Total light transmittance (%) | Crystal grain diameter (μm) | Bending strength (MPa) | Proportion of monoclinic phase after deterioration test (%) | Remarks |
|---|---|---|---|---|---|---|---|---|
| Comparative Example 13 | 10.3 | 0.0117 | 98.86 | — | 0.33 | — | — | Comparative Example |
| Comparative Example 14 | 11.1 | 0.0118 | 99.53 | 21.8 | 0.33 | — | — | Comparative Example |
| Example 29 | 13.5 | 0.0120 | 99.83 | 35.1 | 0.32 | 1080 | 3 | |

TABLE 5-continued

| No. | BET specific surface area (m²/g) | Rate of sintering shrinkage (Δρ/ΔT; g/cm³·°C.) | Relative density, 1400° C. sintering (%) | Total light transmittance (%) | Crystal grain diameter (μm) | Bending strength (MPa) | Proportion of monoclinic phase after deterioration test (%) | Remarks |
|---|---|---|---|---|---|---|---|---|
| Example 30 | 12.1 | 0.0127 | 99.84 | 35.2 | 0.32 | 1100 | 2 | |
| Example 31 | 12.3 | 0.0127 | 99.84 | 35.5 | 0.32 | 1090 | 9 | |
| Example 32 | 13.0 | 0.0128 | 99.88 | 36.9 | 0.32 | 1150 | 11 | |
| Example 33 | 14.7 | 0.0128 | 99.89 | 38.8 | 0.31 | 1200 | 8 | |
| Example 34 | 13.7 | 0.0128 | 99.83 | 35.1 | 0.31 | 1120 | 6 | |
| Example 35 | 13.7 | 0.0129 | 99.83 | 35.2 | 0.32 | 1060 | 4 | |
| Example 36 | 14.8 | 0.0130 | 99.84 | 35.3 | 0.32 | 1080 | 9 | |
| Example 37 | 13.3 | 0.0130 | 99.86 | 36.9 | 0.32 | 1230 | 7 | |
| Example 38 | 14.6 | 0.0131 | 99.84 | 35.4 | 0.32 | 1110 | 2 | |
| Example 39 | 14.1 | 0.0133 | 99.84 | 35.3 | 0.32 | 1140 | 6 | |
| Example 40 | 15.6 | 0.0135 | 99.86 | 37.3 | 0.32 | 1220 | 5 | |
| Comparative Example 15 | 16.4 | 0.0135 | 99.71 | 30.8 | 0.31 | 1020 | — | Comparative Example |
| Comparative Example 16 | 24.8 | 0.0135 | 99.34 | 17.9 | 0.30 | — | — | Comparative Example |

Only the sintered bodies having a relative density of 99.8% or higher had translucency with a total light transmittance of 35% or higher. A relative density of 99.8% or higher is necessary for attaining a transmittance of 35% or higher.

Figure 7:
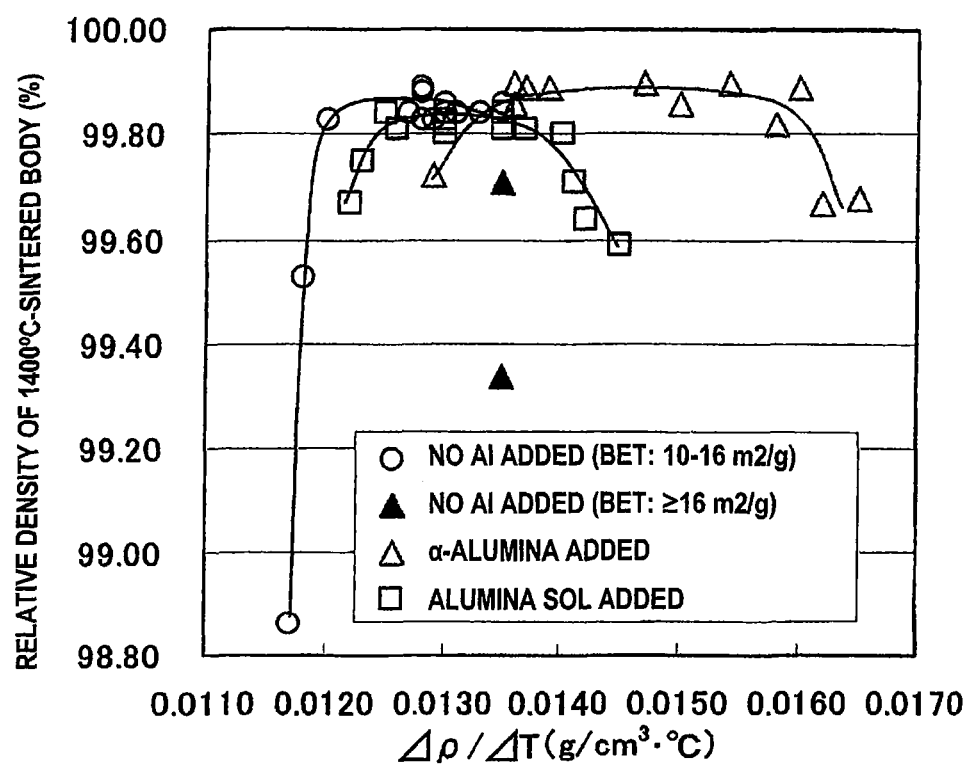
FIG. 7 is a presentation showing relationships between the rate of sintering shrinkage (Δρ/ΔT; g/cm$^3$·° C.) of zirconia containing 0-0.2 wt % alumina and sintered-body relative density.

Relationships between the rate of sintering shrinkage and sinter density according to the invention are shown in FIG. 7.

While the invention has been described in detail and with reference to specific embodiments thereof, it will be apparent to one skilled in the art that various changes and modifications can be made therein without departing from the spirit and scope thereof.

This application is based on a Japanese patent application filed on Apr. 9, 2008 (Application No. 2008-101324), a Japanese patent application filed on Dec. 24, 2008 (Application No. 2008-328498), a Japanese patent application filed on Dec. 24, 2008 (Application No. 2008-328499), and a Japanese patent application filed on Dec. 24, 2008 (Application No. 2008-328500), the contents thereof being herein incorporated by reference.

Industrial Applicability

The translucent zirconia sintered body of the invention has a high density, high strength, and excellent translucency and is hence an excellent zirconia sintered body for use in dental applications, specifically, an excellent sintered body for use as a mill blank for a denture material or the like or as an orthodontic bracket. The powder of the invention for a translucent zirconia sintered body is a powder from which a translucent zirconia sintered body can be produced through normal-pressure sintering without using a large-scale pressure sintering apparatus, for example, one for HIP. Consequently, the invention has a significant industrial value.

The invention claimed is:

1. A translucent zirconia sintered body characterized by comprising zirconia which contains 2-4 mol % yttria as a stabilizer and has an alumina content of lower than 0.1 wt %, and by having a relative density of 99.8% or higher and a total light transmittance, as measured at a thickness of 1.0 mm, of 35% or higher;
   wherein relative density means the value obtained by measuring an actual density ρ by the Archimedes method, determining a theoretical density ρo using the following equation (2), and converting these density values to the proportion (ρ/ρo) times 100(%), and in equation (2), the theoretical density of alumina and the theoretical density of zirconia containing 3 mol % yttria were taken as 3.987 (g/cm3) and 6.0956 (g/cm3), respectively, $$\rho o = 100/[(X/3.987)+(100-X)/6.0956] \quad (2)$$

{X is alumina content (% by weight)}.

2. A translucent zirconia sintered body characterized by comprising zirconia which contains 2-4 mol % yttria as a stabilizer and contains no alumina, and by having a relative density of 99.8% or higher and a total light transmittance, as measured at a thickness of 1.0 mm, of 35% or higher;
   wherein relative density means the value obtained by measuring an actual density ρ by the Archimedes method, determining a theoretical density ρo using the following equation (2), and converting these density values to the proportion (ρ/ρo) times 100(%), and in equation (2), the theoretical density of alumina and the theoretical density of zirconia containing 3 mol % yttria were taken as 3.987 (g/cm3) and 6.0956 (g/cm3), respectively, $$\rho o = 100/[(X/3.987)+(100-X)/6.0956] \quad (2)$$

{X is alumina content (% by weight)}.

3. The translucent zirconia sintered body as claimed in claim 1 which has a crystal grain diameter of 0.20-0.45 μm.

4. The translucent zirconia sintered body as claimed in claim 2 which has a crystal grain diameter of 0.20-045 μm.

5. The translucent zirconia sintered body as claimed in claim 1 which has a monoclinic fraction of 30% or lower after 24-hour immersion in 140° C. hot water.

6. The translucent zirconia sintered body as claimed in claim 2 which has a monoclinic fraction of 30% or lower after 24-hour immersion in 140° C. hot water.

7. The translucent zirconia sintered body as claimed in claim 1 which has a three-point bending strength of 1,000 MPa or higher.

8. The translucent zirconia sintered body as claimed in claim 2 which has a three-point bending strength of 1,000 MPa or higher.

9. A dental material comprising the sintered body as described in claim 1.

10. A dental material comprising the sintered body as described in claim 2.

11. The dental material as claimed in claim 9 which is a denture and/or a denture mill blank.

12. The dental material as claimed in claim 10 which is a denture and/or a denture mill blank.

13. The dental material as claimed in claim 11 which is an orthodontic bracket.

14. The dental material as claimed in claim 12 which is an orthodontic bracket.

* * * * *